United States Patent [19]

Commeyras et al.

[11] Patent Number: 4,677,224

[45] Date of Patent: Jun. 30, 1987

[54] CONTINUOUS PROCESS FOR SYNTHESIZING AN α-AMINO ACID BY CHEMICAL CATALYTIC HYDROLYSIS

[75] Inventors: Auguste Commeyras; Jacques Taillades, both of Castelnau le Lez; Jean Brugidou, Montpellier; Louis Mion, Montpellier; Régine Sola, Montpellier; Robert Pascal, Montpellier; Monique Lasperas, Montferrier sur Lez; Alain Rousset, Montpellier, all of France

[73] Assignee: Centre National de la Recherche Scientifique (CNRS), Paris, France

[21] Appl. No.: 740,803

[22] Filed: Jun. 3, 1985

[30] Foreign Application Priority Data

Jun. 5, 1984 [FR] France .................... 84 08762

[51] Int. Cl.$^4$ .............................................. C07C 99/10
[52] U.S. Cl. ................................. 562/557; 562/575; 422/210
[58] Field of Search ................. 562/575, 559

[56] References Cited

U.S. PATENT DOCUMENTS 4,243,814 1/1981 Pascal .................................. 562/575
4,459,423 7/1984 Doya .................................... 562/575

FOREIGN PATENT DOCUMENTS 1186331 4/1985 Canada ................................ 562/575

*Primary Examiner*—Michael L. Shippen
*Attorney, Agent, or Firm*—Dressler, Goldsmith, Shore, Sutker & Milnamow, Ltd.

[57] ABSTRACT

The device for carrying out the continuous process for synthesizing an α-amino acid incorporates: (a) a vessel (10) for feeding α-amino-nitrile, or one of its salts; (b) a connecting pipe (12), in which a pump (14) is mounted, connecting the feed vessel (10) to (c) a catalysis column (16) containing a carbonyl-containing polymeric resin (18) which is insoluble in basic aqueous medium; (d) a connecting pipe (20) from the catalysis column (16) to (e) a hydrolysis reactor (22), acting simultaneously as a reservoir for the α-amino acid salt formed, and equipped with (f) means for feeding hydroxide ions, comprising a feed vessel (24), a pipe (26) and a pump (28); and (g) a pipe (30) for drawing off the α-amino acid salt formed.

6 Claims, 1 Drawing Figure

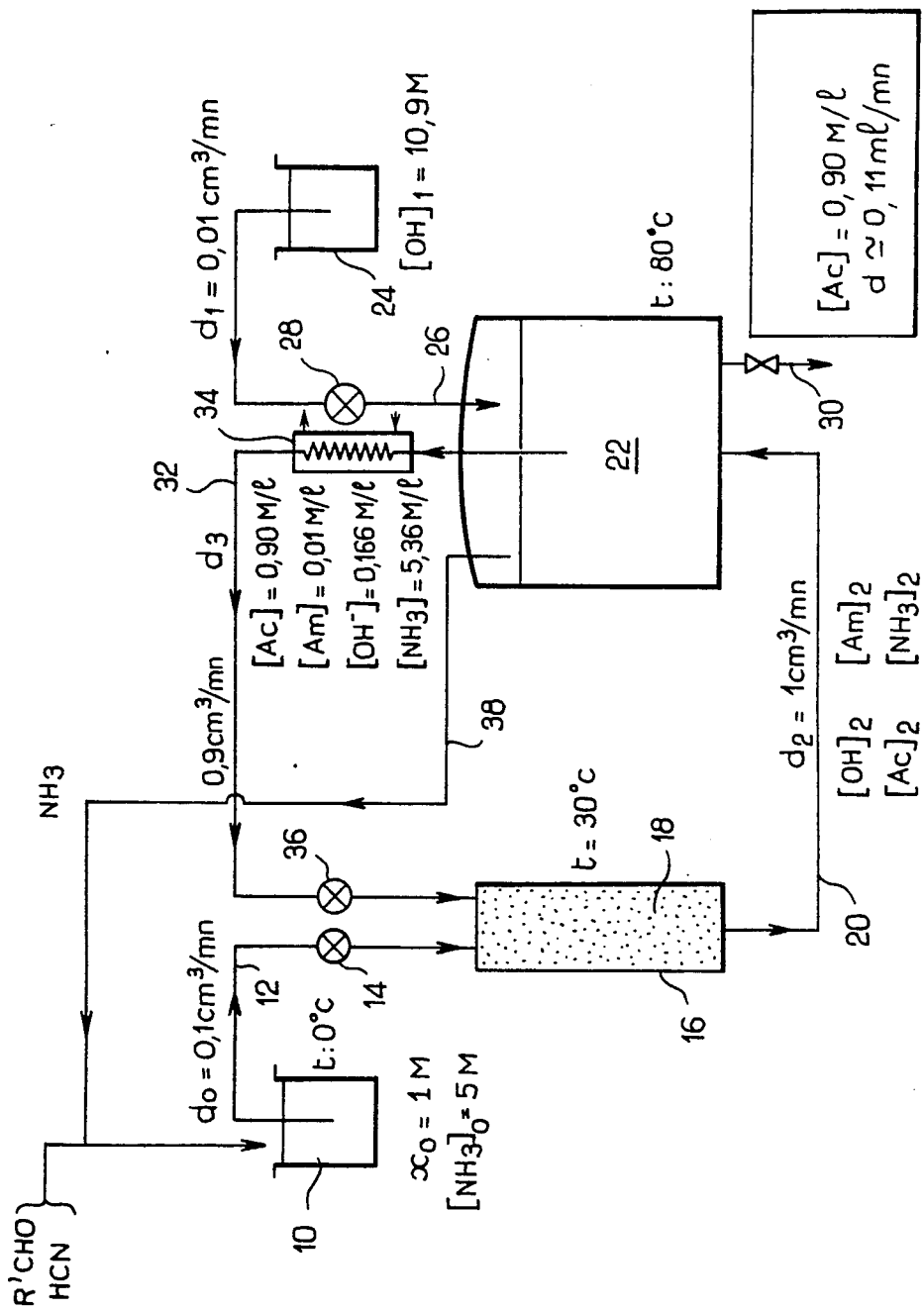

CONTINUOUS PROCESS FOR SYNTHESIZING AN α-AMINO ACID BY CHEMICAL CATALYTIC HYDROLYSIS

TECHNICAL FIELD

The present invention relates to a process for synthesizing an α-amino acid, or one of its salts, by chemical catalytic hydrolysis.

In particular, the present invention has as its subject a continuous process for synthesizing an α-amino acid by chemical catalytic hydrolysis from corresponding α-amino-nitriles, or their salts.

The present invention also relates to a device for implementing this synthesis process.

BACKGROUND ART

It is appropriate to recall in this connection that α-amino acids, especially the so-called essential α-amino acids, are assuming an indisputable and ever-increasing industrial value. Some of them can in fact be used in human or animal medicine, in particular to mitigate certain dietary deficiencies in animal proteins in developing countries, or to supplement the plant proteins used for feeding cattle or poultry. Others of these compounds can also take part, for example, in the composition of soaps or cosmetics.

In the prior art, α-amino acids are prepared from their corresponding aldehyde precursors, by the Strecker reaction or by one of the many modifications applied to the original reaction, and in particular by implementing the process described in French Pat. No. 2,372,797. According to the process of this earlier patent, the intermediate α-amino-nitrile or one of its salts is catalytically hydrolyzed in basic medium, by reacting an aqueous solution containing at least one carbonyl derivative with the said α-amino-nitrile or one of its salts, in the presence of hydroxide ions. Such a process, which is extremely selective and favorable from an economic standpoint, nevertheless requires the separation of the carbonyl catalyst from the reaction medium and possible recycling of the catalyst. Furthermore, in this earlier process, the choice of carbonyl catalyst is greatly limited by the need for it to be stable in homogeneous basic medium.

The French Patent Application published under No. 2,519,973 describes a process for preparing α-amino acids which makes it possible to avoid in part the disadvantages pointed out above. In effect, according to this earlier process, the chemical catalytic hydrolysis of the starting α-amino-nitrile is no longer performed in homogeneous phase but in heterogeneous phase. To this end, a carbonyl catalyst is used which is no longer in solution in the reaction medium, but is a suitable polymeric resin containing carbonyl groups. According to this earlier process, it is observed that, by introducing an α-amino-nitrile or one of its salts into an aqueous solution containing a suspension of an insoluble carbonyl-containing polymeric resin and hydroxide ions, the α-amino-amide corresponding to the starting α-amino-nitrile is obtained very rapidly. The carbonyl-containing resin insoluble in aqueous basic medium can then be separated from the reaction medium by simple filtration or centrifugation, and then be recycled without the need for a regeneration process. Furthermore, instead of the reaction being performed discontinuously, with recycling of the catalyst, the use of a carbonyl-containing polymeric resin enables the process to be carried out continuously by contact of a solution of α-amino-nitrile or one of its salts with the immobilized carbonyl catalyst.

However, the implementation of such a process for preparing α-amino acids by *continuous* chemical catalytic hydrolysis proves to be much more awkward than it appears at first sight. In particular, the gradual decrease in the catalytic activity of the resin is observed, due to poisoning of the terminal carbonyl groups. This substantial decrease in the catalytic activity considerably limits the industrial applications of such a process, and constitutes a major obstacle to the generalized use of the process in the synthesis of α-amino acids, the international market for which is at the height of expansion.

SUMMARY OF THE INVENTION

The present invention has the precise object of overcoming this disadvantage relating to the poisoning of the carbonyl catalyst.

For this reason, the present invention relates to a continuous process for synthesizing an α-amino acid by chemical catalytic hydrolysis, in aqueous basic medium, of an α-amino-nitrile or one of its salts, in the presence of at least one carbonyl derivative, comprising:

(a) a first stage of catalytic hydration of the starting α-amino-nitrile, or one of its salts, to the corresponding α-amino-amide, in the presence of a low concentration of hydroxide ions and using as a catalyst a carbonyl-containing polymeric resin insoluble in basic aqueous medium, (b) a second stage of hydrolysis of the α-amino-amide thus formed to a salt of the corresponding α-amino acid, in the presence of hydroxide ions in substantially equimolar concentration relative to the concentration of the α-amino-amide, in which process a fraction of the volume of the reaction medium of the second stage is withdrawn for the purpose of being recycled, after cooling, to the reaction medium of the first stage, the said fraction being determined so as to provide for dilution of the α-amino-nitrile, or one of its salts, introduced in the medium of the first stage, and to maintain the α-amino-amide concentration in the reaction medium of the first stage below the threshold of poisoning of the carbonyl-containing polymeric resin.

It appears, in fact, that two parameters—hydroxide ion concentration at each of the two stages of the process, and α-amino-amide concentration in the reaction medium of the first stage—are decisively involved in the process according to the invention.

Studies in depth have enabled the present inventors to understand more thoroughly the mechanism of poisoning of the carbonyl-containing resin by the α-amino-amide formed, and to establish the α-amino-amide concentration values compatible with continuous synthesis of the α-amino acid which it is desired to prepare.

Thus, according to another characteristic of the process of the present invention, the threshold of poisoning of the carbonyl-containing polymeric resin is defined by an average α-amino-amide concentration in the reaction medium of the first stage below approximately 0.20 mole/l.

According to the present invention, in a process for synthesizing an α-amino acid in the form of one of its salts, at a concentration of xM from an α-amino-nitrile, or one of its salts, at the same concentration xM, the fraction of the volume of the reaction medium of the second stage, withdrawn and recycled, is determined so that the α-amino-amide concentration in the medium of the first stage is substantially x/10M.

More especially, in a process for synthesizing an α-amino acid in the form of one of its salts at a concentration of 1M from an α-amino-nitrile, or one of its salts, at the same concentration 1M, according to the present invention, the fraction of the volume of the reaction medium of the second stage, withdrawn and recycled, is determined so that the α-amino-amide concentration in the reaction medium of the first stage is substantially decimolar.

According to another characteristic of the process of the present invention, hydroxide ions are introduced in the reaction medium of the second stage in a substantially equimolar amount relative to the α-amino-amide originating from the first stage.

According to another characteristic of the process of the present invention, the amount of hydroxide ions needed for the catalysis originates from the recycling of a fraction of the reaction volume of the second stage.

The studies which enable the optimal conditions, defined above, to be established for carrying out the continuous synthesis process according to the present invention are described below.

As regards the carbonyl-containing polymeric resins suitable for carrying out this process, reference will be made, without these being in any way limitative, to polymeric resins bearing side chains with a terminal carbonyl group, as well as to the respective process for preparation thereof, described in French Patent Application No. 2,519,973.

The catalytic activity of these resins was tested in a continuous assembly. Following these preliminary trials, the poly(N-acylpiperidone) resin, the active unit of which is illustrated by the formula I, was adopted:

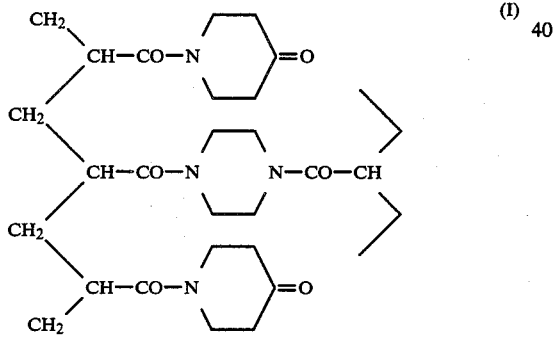
(I)

This resin is obtained by polymerization of acryloyl-piperidone,

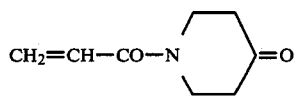

(80%), and crosslinked with 20% of N,N'-bis(acryloyl-piperazine):

It proved very efficient (capacity 2.5 meq/g, after conditioning in basic medium), and it is, moreover, relatively easy to prepare.

The mechanism of the catalysis is shown in simplified fashion below in Scheme 1. The reaction is reduced kinetically to two stages, on the one hand the formation of the intermediate imine, and on the other hand hydrolysis of the imine with regeneration of the catalyst, and this is the rate-determining stage.

For convenience of analysis, especially by NMR, the mechanism of this catalysis was studied mainly using α-aminopropionitrile—formula II—as substrate. This compound is, however, representative as regards reactivity of (α-amino)methylmercaptobutyronitrile—formula III—a precursor of methionine.

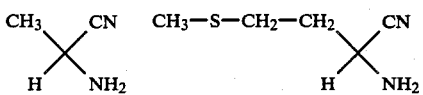

(II)                (III)

SCHEME 1

Mechanism of the catalytic hydration process.

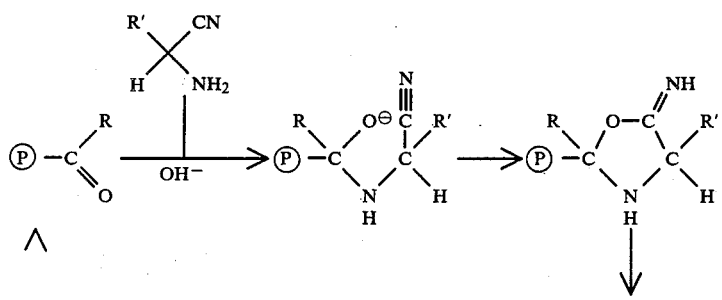

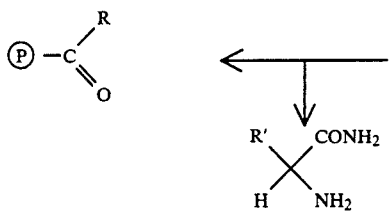

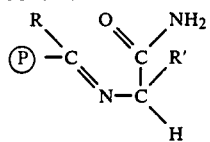

Ⓟ: polymer matrix

The interpretation of the catalytic process on carbonyl-containing resin, which is endowed with a complex kinetic behavior, rests on the principle of a distribution of reactivity which results from the non-equivalence of the catalytic sites bound to the polymer.

It is observed that, at an α-amino-nitrile concentration of 0.1 molar, the catalyst (I) has satisfactory catalytic activity, especially superior to that of acetone. Under these conditions, and using a caustic soda concentration of the order of 0.1 mole/l and at 25° C., the catalyst quantitatively converts α-amino-nitrile to α-amino-amide, not undergoing any significant ageing.

For molar α-amino-nitrile concentrations, a gradual decrease in the catalytic activity is observed. The origin of this poisoning of the catalyst corresponds to the formation of the 4-imidazolidinone, according to a mechanism which depends on the nature of the carbonyl compound. In the particular case of ketone compounds, the imidazolidinone is formed from the imine intermediate according to the reaction scheme:

catalytic reaction and the formation of the imidazolidinone.

In the hydration reaction, the slow stage is the hydrolysis of the imine; its activation energy is of the order of 16 kcal/mole, that is to say substantially greater than that of the first stage, which is overall only 3 kcal/mole.

In consequence, to avoid saturation of the catalytic sites and increase the turnover of the catalyst, it appears logical to increase the reaction temperature to accelerate the 2nd stage. Furthermore, this would favor an increase in the proportion of carbonyl formed relative to the hydrated form and, as a corollary, would favor an increase in reactivity.

Nevertheless, it is not possible to confine oneself to this observation alone, since other phenomena are, in fact, involved.

In the first place, under the basic conditions required for hydration of the α-amino-nitrile, the latter decomposes slowly ($k_D = 3.3 \times 10^{-3}$ min$^{-1}$ for R'=CH$_3$). According to the reaction:

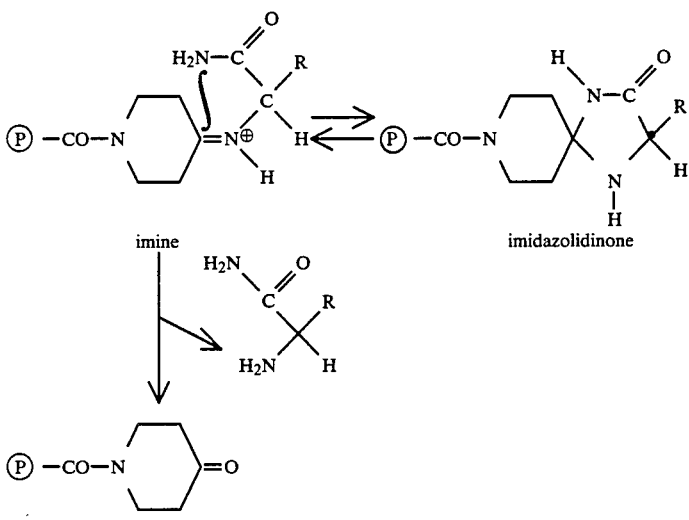

where Ⓟ denotes the polymer matrix.

This side reaction is promoted by an increase in the α-amino-nitrile concentration, which leads to the accumulation of the α-amino-amide imine on the catalytic sites of the resin.

Since the reaction is balanced, poisoning of the catalyst is reversible. Thus, a resin thus inactivated can be regenerated, by passing water over the latter at 80° C. Under these conditions, the imidazolidinone is hydrolyzed to α-amino-amide while the resin recovers its initial catalytic activity.

To define the optimal conditions for using the catalyst, account should hence be taken of the requirements linked not only to the catalytic process itself, but also to those relating to the side reactions, namely, the self-

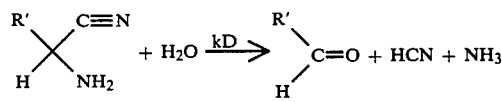

which is independent of the pH but strongly accelerated by a temperature rise ($E_A = 23$ kcal/mole for R'=CH$_3$).

The aldehyde which appears in the medium can, on account of its high reactivity, play the role of catalyst of hydration of the nitrile $(k'_H = 4 \times 10^{-3} \text{ min}^{-1} \text{ moles}^{-2} \text{ l}^2 \text{ for } R' = CH_3)$.

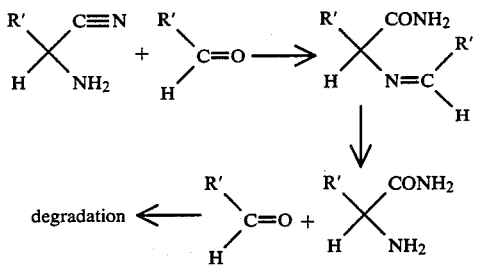

Contrary to appearances, this reaction is deleterious, since the aldehyde, in basic medium, is degraded rapidly by various reactions (addition to the amines present in the medium, aldolization, crotonization), considerably lowering the overall yield of the reaction (70% in the case of α-(amino)methylmercaptobutyramide). It is hence necessary to replace the self-catalytic reaction by the catalytic process, and hence to work under conditions of maximum column efficiency, that is to say in such a way that the ratio ϵ is as large as possible.

$$\epsilon = \frac{\text{number of catalytic sites}}{\text{number of substrate molecules}} = \frac{m \times Cp_{C=O}}{Vr \times \left[ \begin{array}{c} R' \quad CN \\ \diagdown \diagup \\ \diagup \diagdown \\ H \quad NH_2 \end{array} \right]}$$

m: mass of resin
$Cp_{C=O}$: capacity of the resin
Vr: residual volume of the column (occupied by the solution)

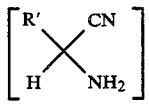

=amino-nitrile concentration in the solution injected.

For a given resin column, correctly packed, the only possibility of increasing the ratio ϵ is to decrease the α-amino-nitrile concentration.

It follows from this observation that it is not possible to work with a high α-amino-nitrile concentration. This limitation is akin to that imposed by the imidazolidinone formation reaction, which involves not using a high concentration of α-amino-amide, and hence of α-amino-nitrile which is its precursor.

It consequenty follows from this analysis of the conditions for using the supported carbonyl catalysts:

Firstly, that the reaction temperature must be limited. An acceptable compromise is in the region of 30° C.

Secondly, that the α-amino-nitrile concentration must not exceed a value of the order of 0.2 mole/liter, at the risk of promoting the side reactions with, in consequence, a decrease in the yield of the reaction and poisoning of the catalyst, which, while reversible, is nevertheless to be avoided.

These conditions for using the catalyst conflict with a requirement of an economic nature, which imposes working on relatively concentrated α-amino-nitrile solutions in order to obtain, at the final stage, the α-amino acid at an acceptable concentration, of the order of 1 mole/liter. It is, in effect, important to avoid costly concentration operations and to limit the sizes of the installation.

To attenuate these problems, and reconcile the requirements imposed by the reaction with those of an economic nature, the present invention proposes a technical solution which consists of diluting on the catalysis column the α-amino-nitrile with a solution of the corresponding α-amino acid. The principle of this continuous processor synthesizing α-amino acids is shown in the attached figure, which illustrates schematically a particular embodiment of the installation according to the invention. The flow rates, concentrations and temperatures which appear in this figure correspond to the preparation of alanine.

These studies relating to this principle of continuous synthesis of α-amino acids by chemical catalytic hydrolysis led to the development of a device for carrying out this process in an optimal manner.

For this reason, another subject of the present invention relates to a device for carrying out the continuous process for synthesizing an α-amino acid, the said device incorporating:

(a) a vessel 10 for feeding α-amino-nitrile, or one of its salts,
(b) a connecting pipe 12, in which a pump 14 is mounted, connecting the feed vessel 10 to
(c) a catalysis column 16 containing a carbonyl-containing polymeric resin 18 which is insoluble in basic aqueous medium,
(d) a connecting pipe 20 from the catalysis column 16 to
(e) a hydrolysis reactor 22, acting simultaneously as a reservoir for the α-amino acid salt formed, incorporating means of heating and stirring the reaction medium, and equipped with
(f) means for feeding hydroxide ions, comprising a feed vessel 24, a pipe 26 and a pump 28, and
(g) a pipe 30 for drawing off the α-amino acid salt formed, the said device containing, in addition, a recycling pipe 32 equipped with a condenser 34 and a pump 36, the said recycling pipe connecting the hydrolysis reactor 22 to the inflow pipe of the catalysis column 16 so as to provide for the dilution of the stream of α-amino-nitrile, or one of its salts, feeding the said catalysis column.

According to another characteristic of the said device, pumps 14, 28 and 36, mounted respectively in the pipes for feeding E-amino-nitrile, or one of its salts, 12,
for feeding hydroxide ions 26, and
for recycling 32 the reaction medium of the second stage, are centrifugal pumps having adjustable flow rates.

According to another characteristic of the same device, the hydrolysis reactor 22 has, in addition, a pipe 38 which opens into the gaseous top of the said reactor and is designed to recycle ammonia released during the second stage, for the purpose of using it for preparing in situ the starting α-amino-nitrile or one of its salts.

According to another characteristic, the device of the present invention incorporates at least a second catalysis column mounted in parallel with the first column 16, to operate alternately with the latter, each of these columns being equipped with means suitable for regenerating the carbonyl-containing polymeric resin and with a valve system enabling the catalysis columns to operate alternately.

The means suitable for regenerating the carbonyl-containing polymeric resin incorporate a circuit for washing with water, comprising (i) an inlet for water heated to approximately 80° C., (ii) a regeneration column in which a sulfonic resin is arranged to bind the amide drawn into the said circuit, the said regeneration column being connected by (iii) connecting pipes at the inlet and outlet of the catalysis column.

The sulfonic resin can itself be regenerated by elution with ammonia.

The detailed operation will be explained below but, in a simplified manner, it takes place in the following fashion:

The α-amino-nitrile is stored at a concentration of 1 mole/liter in the presence of 5M ammonia and at low temperature (0° C.), which provides for its optimum thermodynamic stabilization.

It is introduced continuously into the hydration catalysis column packed with carbonyl-containing resin, after being diluted by recycling of the α-amino acid in basic solution. As it leaves the column, the α-amino-amide formed by hydration of the nitrile, and the concentration Am2 of which is of the order of 0.1 mole/l is introduced into the hydrolysis reactor brought to 80° C., wherein it is hydrolyzed to the α-amino acid. The caustic soda needed for the hydrolysis is added continuously in very concentrated solution and at a very low flow rate. The ammonia, on the one hand introduced into the reaction, and on the other hand formed by hydrolysis of the amide, can readily be recovered and re-used to synthesize, with the aldehyde and hydrocyanic acid, the α-amino-nitrile.

The α-amino acid produced, in salt form, is drawn off from the hydrolysis reactor at a flow rate almost equal to that of the α-amino-nitrile introduced (if the extremely low flow rate of the caustic soda solution added is ignored). The concentration of the α-amino acid thus synthesized is of the order of 1 mole/liter.

By way of illustration, a few particular examples of continuous synthesis of α-amino acids by the chemical catalytic hydrolysis process will be mentioned below, using the installation according to the present invention.

EXAMPLE I

CONTINUOUS PREPARATION OF ALANINE FROM α-AMINO-PROPIONITRILE

A. DETERMINATION OF THE WORKING CONDITIONS

The results of the basic study in depth of the process of conversion of an aldehyde to the corresponding α-amino acid, both in respect of the reaction mechanisms and in respect of the various kinetic parameters, made it possible to predict the values of the different arameters (flow rates, concentrations, temperatures) affecting the satisfactory operation of the pilot installation.

1. Hydration reaction (catalysis)

A column (height 250 mm, diameter 6 mm) thermostated at 30° C. is used, containing 1.5 g of N-acylpiperidone resin (I), which corresponds to 5.5 g of wet resin

BRIEF DESCRIPTION OF THE DRAWINGS

The principle of this continuous process for synthesizing alpha-amino acids is shown in the attached FIGURE, which illustrates schematically a particular embodiment of the installation according to the invention. The flow rates, concentrations and temperatures which appear in this FIGURE correspond to the preparation of alanine.

DETAILED DESCRIPTION OF THE INVENTION

The hydration reaction of the α-amino-nitrile is under chemical control; the rate of disappearance of the α-amino-nitrile is proportional to the number of carbonyl sites in the catalyst, and is of the 1st order with respect to the α-amino-nitrile and hydroxyl ion concentrations.

For the combination of the following conditions:
1.5 g of piperidone resin (I)
$OH^- = 0.15M$

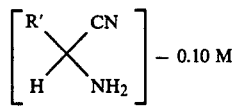
$$\left[ \begin{array}{cc} R' & CN \\ & \times \\ H & NH_2 \end{array} \right] - 0.10\,M$$

solution volume: 5 cm³
t = 20° C., the half-time of the reaction of disappearance of the α-amino-nitrile, determined "batchwise" is of the order of one minute. It can hence be considered that the disappearance of the nitrile will be complete in 3 minutes, or $3 \times t_{\frac{1}{2}}$.

These results can be transferred to the continuous operation of the column. The α-amino-nitrile concentration at the outflow from the column "C" is related to the α-amino-nitrile concentration at the head of the column, "Co", by the relation:

$$C = Co.e^{-K\tau}$$

τ = residence time in the column
K = experimental rate const.

The flow rate "f" of the nitrile in the column can be determined approximately for complete hydration to be achieved.

$$\tau = \frac{V}{d} \quad f = \frac{5}{1.5} = d\; 3.3\; cm^3/min.$$

The use of a flow rate of 1 cm³/min enables there to be a sufficient safety margin to take account, in particular of the partial occupation of the catalytic sites by the α-amino-amide imine.

2. Hydrolysis reaction

The rate of hydrolysis of the α-amino-amide to the α-amino acid in basic medium is of the first order with respect to the amide and hydroxyl ion concentrations. The activation energy of the reaction is 13.5 kcal/mole and the rate constant $K = 2.9 \times 10^{-2} M^{-1}$ at 35° C. The volume V of the hydrolysis reactor can be determined from the inflow and outflow mass balance of the α-amino-amide in the reactor operating in the stationary state. The variables involved in the equations below are defined in the scheme:

$$\begin{array}{ccc} f_2[Am]_2 & = & f_3[Am] & + V \times k\,[OH^-]\,[Am] \\ \text{amide introduced} & & \text{recycled residual amide} & \text{hydrolyzed amide} \end{array}$$

or:

$$f_2 \frac{[Am]_2}{[Am]} = f_3 + V \times k[OH^-]$$

-continued $$V = f_2 \frac{[Am]_2}{[Am]} - f_3 \times \frac{1}{K[OH^-]}$$

If a degree of conversion of 90% is fixed at the outset, $$\frac{[Am]_2}{[Am]} = 10$$

The various parameters taking part in the equation can be determined as follows:

(a) flow rates:

Following the calculation of the residence time in the catalysis column, the flow rate was fixed at 1 ml/minute.

Hence: $f_2 = 1$ ml/min.

Furthermore, the ratio $(f_o/f_2)$ is chosen to be equal to 1/10, so that the nitrile concentration in the catalysis column is 0.1 molar, and consequently $f_o = 0.1$ ml/min.

The recycling flow rate will hence be $f_3 = f_2 - f_o$, so $f_3 = 0.90$ ml/min.

(b) Determination of the concentration of the caustic soda solution in the hydrolysis reactor.

The mass balance for the caustic soda at the inflow and outflow of the catalysis column can be written in the form:

$$[f_2 - f_o][OH^-] = f_2[OH^-]_2$$

whence:

$$[OH^-] = \frac{f_2}{f_2 - f_o} [OH^-]_2$$

The value is fixed at the beginning: $[OH^-]_2 = 0.15$ mole/l, consequently:

$$[OH^-] = 0.15 \times (1/1 - 0.1) = 0.116 \text{ mole/l}.$$

(c) Volume of the hydrolysis reactor:

In order to limit the volume of the hydrolysis reactor, it was chosen to work at 80° C. (this value is not limitative). Under these conditions, the rate constant of hydrolysis K is of the order of 0.36 $M^{-1}$ min$^{-1}$.

The volume of the reactor is given by the previously established expression.

$$V = \left[ f_2 \times \frac{[Am]_2}{[Am]} - f_3 \right] \times \frac{1}{k[OH^-]}$$

$$V = [1 \times 10 - 0.9] \times \frac{1}{0.36 \times 0.166} = 152 \text{ cm}^3$$

$$V = 152 \text{ cm}^3$$

(d) Residual amide concentration at the outflow of the hydrolysis reactor:

The following relations express the mass balance relating to the α-amino-amide in the catalysis column and in the hydrolysis reactor, respectively.

$$\underset{\text{nitrile introduced}}{f_o x_o} + \underset{\text{amide recycled}}{(f_2 - f_o)[Am]} = \underset{\text{amide formed}}{f_2[Am]_2}$$

-continued $$\underset{\text{amide introduced}}{f_2[Am]_2} = \underset{\text{amide recycled}}{f_3[Am]} + \underset{\text{acid formed}}{Vk[OH^-][Am]}$$

making these equal, there is obtained:

making these equal, there is obtained:

$$f_3[Am] + Vk[OH^-][Am] = f_o x_o = (f_2 - f_o)[Am]$$

$$[Am] = \frac{f_o x_o}{f_3 - f_2 = f_o + Vk[OH^-]}$$

but $f_3 = f_2 + f_1$ $$[Am] = \frac{f_o x_o}{f_o + f_1) + Vk[OH^-]}$$

$f_1$ has the very low value of 0.01/min, to avoid dilution of the medium.

$$[Am] = \frac{0.1 \times 1}{(0.1 + 0.01) + 152 \times 0.36 \times 0166}$$

$$[Am] = 0.01 \text{ mole/l}$$

(e) Calculation of the concentrations of the caustic soda solution added continuously:

From the following relations which express the mass balance for the caustic soda at the inflow and outflow of the catalysis column and hydrolysis reactor, respectively:

$$\underset{\text{caustic soda introduced}}{(f_2 - f_o)[OH^-]} = \underset{\text{caustic soda flowing out}}{f_2[PH^-]_2}$$

$$\underset{\text{caustic soda added}}{f_1[OH]_1} + \underset{\text{caustic soda flowing in}}{f_2[OH^-]_2} = f_3[OH^-] +$$

$$\underset{\text{caustic soda recycled}}{V \times k} \times \underset{\text{caustic soda consumed}}{[OH^-][Am]}$$

$$f_1[OH^-]_1 + (f_2 - f_o)[OH^-] =$$

$$f_3[OH^-] + V \times k \times [OH^-][Am]$$

$$f_3 = f_1 + f_2$$

$$f_1[OH^-] = (f_1 - f_2) - (f_2 - f_o[OH^-] + VK[OH^-][Am]$$

$$f_1[OH^-]_1 = [OH^-](f_1 + f_o) + V \times k \times [Am]$$

$$[OH^-]_1 = \frac{[OH^-]}{d_1}(f_1 + f_o) + VK[Am]$$

$$[OH^-]_1 = \frac{0.166}{0.01}[(0.01 + 0.1) + 152 \times 0.36 \times 0.01]$$

$$[OH^-]_1 = 10.9 \text{ moles/liter}.$$

(f) Assessment of the ammonia concentration in the hydrolysis reactor:

As above, the mass balance is written for the ammonia in the catalysis column and in the hydrolysis reactor, respectively.

$$f_o[NH_3]_0 + (f_2 - f_o)[NH_3] = f_2[NH_3]_2$$

$$V \times k \times [OH^-][Am] + f_2[NH_3]_2 = f_3[NH_3]$$

combining these two relations, there are arrived at:

$$[NH_3] = \frac{1}{f_1 + f_0}(f_0[NH_3]_0 + V \times k \times [OH^-][Am])$$

$$[NH_3] = \frac{1}{0.1 + 0.01}(0.1 \times 5 + 152 \times 0.36 \times 0.166 \times 0.01)$$

$[NH_3] = 5.36$ moles/liter.

(h) Assessment of the concentration of α-amino acid formed

The mass balance for the α-amino acid in the hydrolysis reactor and in the catalysis column, respectively, is expressed by the following relations:

$$(f_2 - f_0)[Ac] = f_2[Ac]_2$$

$$V \times k \times [OH^-][Am] + f_2[Ac]_2 = f_3[Ac]$$

on the basis of the these two relations, there may be written:

$$(f_3 - f_2 + f_0)[Ac] = V \times k[OH^-][Am]$$

moreover, it has previously been established that:

$$V \times k \times [OH^-][Am] = f_0 x_0 - (f_0 + f_1)[Am]$$

furthermore $f_3 = f_2 + f_1$
hence:

$$[Ac] = \frac{f_0 x_0}{f_1 f_0} - [Am]$$

$$[Ac] = \frac{0.1 \times 1}{0.01 + 0.1} - 0.01 = 0.899 \simeq 0.90 \text{ mole/l.}$$

Under the working conditions adopted, the concentration of the amino acid formed is equal to 90% of the concentration of the α-amino-nitrile introduced.

The α-amino acid is drawn off at a flow rate F: $f_0 + f_1 = 0.11$ ml/minute.

(i) Monitoring of operation of the installation:

The monitoring of the operation is carried out at different levels and by several methods.

The effluents from the catalysis column are analyzed by NMR. In the alanine series, it is checked that the hydration of the α-amino-nitrile to amide is complete. At the pH used, the signals of the methyl group of the amino acid, the α-amino-nitrile and the α-amino-amide are, in fact, separate.

Likewise, the operation of the hydrolysis reactor is monitored by NMR.

The purity of the α-amino acid is also monitored by TLC (SiO$_2$; eluant, 70:30—2-propanol/34% strength ammonia; visualizing agent, ninhydrin).

Using a potentiometric titrator, the following are assayed successively with HCl (1N), on 1-cm$^3$ test samples diluted with 50 cm$^3$ of methanol:hydroxyl ions [OH$^-$], ammonia [NH$_3$], the amino function of the amino acid and then the carboxyl groups of the α-amino acid. The ammonia can also be driven off beforehand. The fact of obtaining:

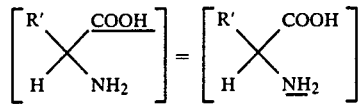

constitutes an additional criterion of purity.

B. CONTINUOUS SYNTHESIS OF ALANINE:

The hydrolysis reactor is charged with 150 cm$^3$ of a solution:
0.88M with respect to sodium alaninate,
0.166M with respect to caustic soda,
5.4M with respect to ammonia, so as to attain the stationary state immediately. It is brought to 80°–85° C.

1M α-aminopropionitrile, in 5M ammoniacal solution stored at 0° C., is injected at a flow rate $x_0 = 0.10$ ml/min. It is diluted as it enters the catalysis column with the recycled basic α-amino acid solution at a flow rate of 0.9 ml/min. 10.9M caustic soda feeds the hydrolysis reactor at a flow rate $f_1$ of 0.01 ml/min.

After more than 150 hours of continuous operation, the efficiency of the catalysis column maintained at 29°–30° C. remains unchanged.

The yield determined by assay of the amino acid drawn off is 96%.

During this period, there are collected:
$150 \times 60 \times 0.1 = 900$ ml of 0.863M sodium alaninate solution.

EXAMPLE II:

CONTINUOUS PREPARATION OF METHIONINE FROM (α-HYDROXY)METHYLMERCAPTOBUTYRONITRILE:

The process is the same as is used in the case of alanine (Example I). However, molar (α-amino)methylmercaptobutyronitrile is obtained by heating (α-hydroxy) methylmercaptobutyronitrile to 45° C. for 1 hour 30 min. in 15N ammonia solution. It is stored at a temperature of 35° C., and injected at a flow rate of 0.06 ml/minute in the catalysis column thermostatted at 37° C. and containing 2 g of piperidone resin ($C_{pC=O} = 2.4$ meq./g).

The α-amino-nitrile is diluted as it enters the catalysis column with the recycled 1M basic α-amino acid solution 0.15N with respect to caustic soda, at a flow rate of 0.92 ml/minute. The hydrolysis reactor is maintained at 90° C.

The yield determined by assay of the carboxyl group of the amino acid is 95%.

The monitoring of the operation is performed by NMR. At the pH used, the signals of the methyl group of the α-amino-nitrile and the α-amino-amide are sufficiently separated to enable the hydration reaction to be monitored.

EXAMPLE III:

COMPARISON OF THE "CATALYTIC PROCESS" WITH THE BUCHERER PROCESS:

For a better appraisal of the efficiency of the catalytic process, it was found to be useful to compare it with the "BUCHERER" process which is currently used industrially for synthesizing methionine, and which is based on the Bucherer-Bergs reaction.

These two processes, the principal phases of which are collated in Table 1, both operate by way of the same reaction intermediate, namely the α-amino nitrile, and lead to the sodium salt of the α-amino acid, either by way of the hydantoin intermediate (Bucherer process) or by way of the α-amino-amide intermediate (catalytic process).

1. Yield:

It was observed that, in the pilot installation described above, the yield of alanine sodium salt relative to the starting acetaldehyde is of the order of 96%. In the Bucherer process, the yield, likewise, of alanine sodium salt is situated, depending on the case, at between 85 and 90% relative to the acetaldehyde.

TABLE 1

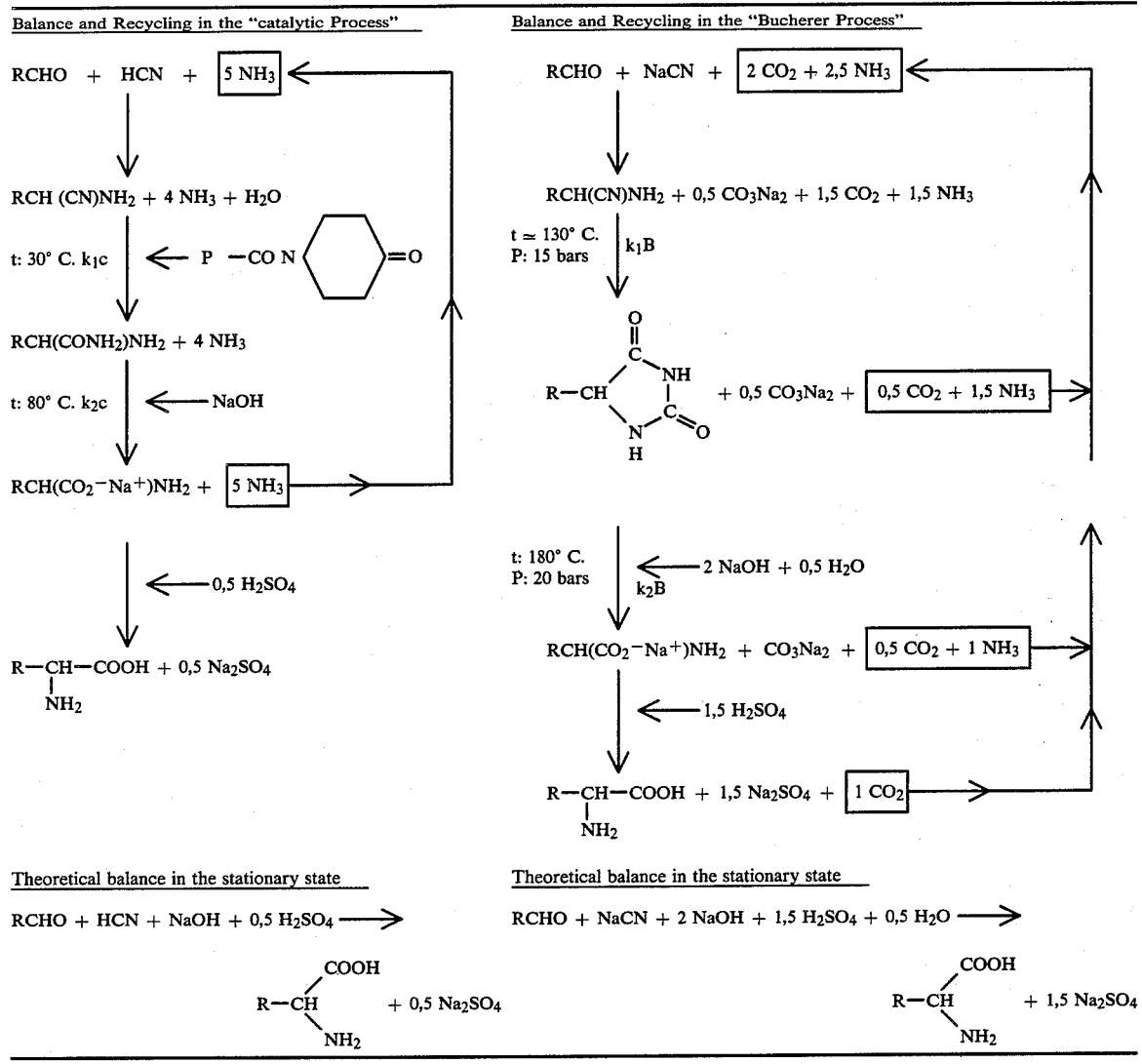

In the catalytic process, the α-amino-nitrile is synthesized beforehand, before being catalytically hydrated. In contrast, in the Bucherer process, the two stages of formation of the α-amino-nitrile and the hydantoin are performed in the same reaction medium, and this does not only have advantages. In effect, to obtain a satisfactory rate of formation of the hydantoin, relatively high temperature conditions must be applied, and these thermodynamically favor the decomposition products of the α-amino-nitrile.

The comparison will bear on four important aspects of these two processes:
  yield,
  reactivity,
  overall material balance,
  recycling of the synthesis intermediates,
and these are analyzed successively below.

2. Reactivity:

The kinetic comparison of the two processes can be carried out from the intermediate α-amino-nitrile common to both processes, up to the formation of the sodium salt of the amino acid.

The rate of each of the processes is regulated on the one hand by the rates of formation ($k_{1B}$) and hydrolysis ($k_{2B}$) of the hydantoin, and on the other hand by the rates of formation ($k_{1C}$) and hydrolysis ($k_{2C}$) of the α-amino-amide.

The values of these rates constants wil be compared exclusively in the case of alanine, but it is known that they are representative, to one order of magnitude, of the reactivity of the methionine precursor.

Formation of the hydantoin—$k_{1B}$:

The rate of formation of the hydantoin is of the first order with respect to the concentration of the carbamate of the α-amino-nitrile. On the assumption (not technically feasible) that the conditions (partial pressure of $CO_2$, pH, insignificant decomposition of the α-amino-nitrile) used are the most favorable for which the α-amino-nitrile is completely in the form of the carbamate, the values of the rate constant $k_1B$ for the appearance of the hydantoin, in terms of the temperature, are:

| t | $k_1B$ min$^{-1}$ |
|---|---|
| 30° C. | $0.028 \times 10^{-2}$ |
| 50° C. | $0.4 \times 10^{-2}$ |
| 75° C. | $5 \times 10^{-2}$ |
| | $E_a = 23$ kcal/mole |

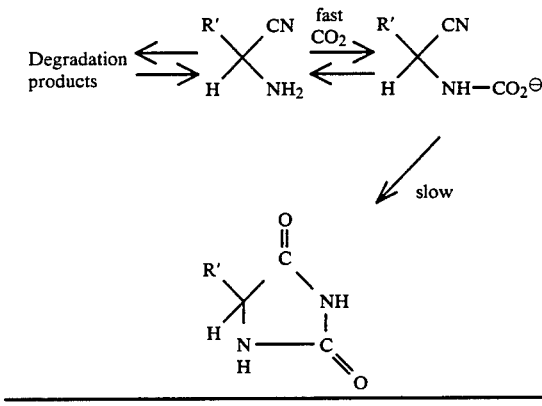

Hydrolysis of hydantoin $k_2B$

The rate of this reaction is of the first order with respect to the hydantoin concentration. In sufficiently basic medium ($[OH^-]=0.1N$), the hydantoin a is predominantly in ionic form b. The slow stage of the hydrolysis reaction, independently of the pH of the reaction medium, is the attack of $OH^-$ on the un-ionized hydantoin:

| t | $k_2B$ min$^{-1}$ |
|---|---|
| 60° C. | $6.5 \times 10^{-3}$ |
| 80° C. | $3 \times 10^{-2}$ |
| | $R' = CH_3$ |
| | $E_A = 18$ kcal/mole |

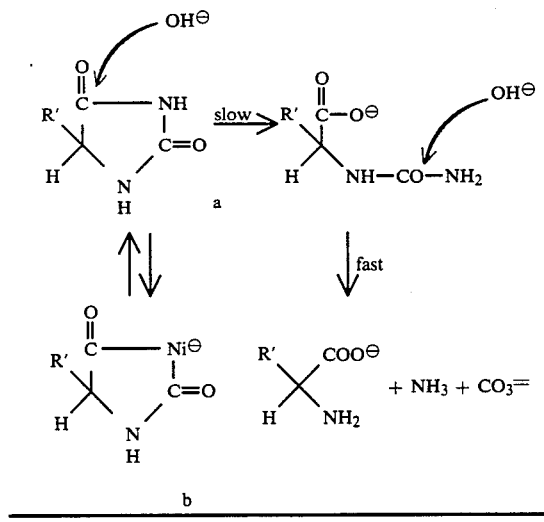

Catalytic hydration of the α-amino-nitrile $k_1C$:

The rate of catalytic hydration of the α-aminominonitrile, which is proportional to the mass of the carbonyl-containing resin, is of the first order with respect to the concentration of α-amino-nitrile and of hydroxy ions. It was thus possible to determine in "batch" tests the values of the rate constant at different temperatures.

| $R' = CH_3$ | t | $k_1C$ M$^{-1}$ min$^{-1}$ | (per gram of resin) |
|---|---|---|---|
| | 8° C. | 3.26 | $E_A = 3$ kcal/mole. |
| | 20° | 4.08 | |
| | 34° | 5.31 | |

Basic hydrolysis of α-amino-amide—$k_2C$:

This reaction is similar, from the mechanistic point of view, to the basic hydrolysis of monofunctional amides. It is of the first order with respect to the concentrations of α-amino-amide and of hydroxyl ions.

| t | $k_2C$ M$^{-1}$ min$^{-1}$ | |
|---|---|---|
| 15° C. | 0.0063 | $E_A = 13.5$ kcal/mole. |
| 35° | 0.029 | |
| 80° | 0.36 | |

The table below collates the values of the different rate constants defined above.

| Bucherer process | Catalytic process |
|---|---|
| $k_1B$: 0.05 min$^{-1}$ (75° C.) | $k_1C = 4$ M$^{-1}$ min$^{-1}$/g (30° C.) |
| $k_2B$: 0.03 min$^{-1}$ (80° C.) | $k_2C = 0.36$ M$^{-1}$ min$^{-1}$ (80° C.) |

Direct comparison of the numerical values of the rate constants $k_1B$ and $k_1C$ is relatively difficult. It is, however, clear that the formation of the α-amino-amide performed at room temperature ($E_a$ almost zero) is substantially faster than that of the hydantoin.

Thus, the half-time of formation of the hydantoin at 75° C. is of the order of 15 min. (optimum theoretical value not taking account of the balanced decomposition of the α-amino-nitrile).

Under representative conditions ([nitrile]=-[$OH^-$]=0.05M, mass of resin 1.5 g, $Cp_{C=O}=1.4$ meq./g, solution volume 15 cm$^3$, t=20°), the half-time of the α-amino-nitrile hydration reaction is only 2 minutes.

As regards the values of the rate constants $k_2C$ and $k_2B$ for formation of sodium alaninate in 1N caustic soda, these are directly comparable. It is observed that, under the condition specified (80° C.), the hydrolysis of the α-amino-amide is 10 times faster than that of the hydantoin. This difference diminishes somewhat at a higher temperature, as a result of the observed difference between the activation energies of the two reactions.

3. Overall material balance:

The material balance is substantially in favor of the catalytic process. In effect, only 0.5 mole of $Na_2SO_4$, originating exclusively from the neutralization of the sodium alaninate, is formed per mole of amino acid produced. In contrast, the Bucherer process, which uses NaCN as a reagent instead of HCN, leads to the formation of 1.5 mole of $Na_2SO_4$, originating from the neutralization of the sodium alaninate and of the sodium carbonate formed during the hydrolysis of the hydantoin, per mole of amino acid produced.

This comparison, on the basis of the formation of non-exploitable by-products ($Na_2SO_4$), acquires full significance when the substantial tonnage of methionine currently produced by the Bucherer process is taken into account.

4. Recycling of the synthesis intermediates:

If the advantages of the catalytic process are clearly apparent both as regards reactivity and as regards the amount of by-products formed, the simplicity of operation as compared with the Bucherer process is still more obvious.

The catalytic process only requires a single, relatively simple recycling of ammonia, whereas the Bucherer process involves three successive recyclings of two products ($CO_2$ and $NH_3$) at the three reaction stages.

This analysis clearly demonstrates the advantages linked to the process which is the subject of the present invention.

We claim:

1. In a continuous process for synthesizing an α-amino acid by chemical catalytic hydrolysis, in aqueous basic medium, of an α-amino-nitrile or one of its salts, soluble in said aqueous basic medium, in the presence of at least one carbonyl derivative in the form of a carbonyl-containing polymeric resin insoluble in said aqueous basic medium, the improvement wherein said synthesis is carried out in:

(a) a first stage of catalytic hydration of the starting α-amino-nitrile, or one of its salts, to the corresponding α-amino-amide, in the presence of a low concentration of hydroxide ions and using as a catalyst said carbonyl-containing polymeric resin, and (b) a second stage of hydrolysis of the α-amino-amide thus formed to a salt of the corresponding α-amino acid, in the presence of hydroxide ions in substantially equimolar concentration relative to the concentration of the α-amino-amide, in which process a fraction of the volume of the reaction medium of the second stage is withdrawn for the purpose of being recycled, after cooling, to the reaction medium of the first stage, the said fraction being determined so as to provide for dilution of the α-amino-nitrile, or one of its salts, introduced in the medium of the first stage, and to maintain the α-amino-amide concentration in the reaction medium of the first stage below the threshold of poisoning of the carbonyl-containing polymeric resin.

2. Synthesis process as claimed in claim 1, in which the said threshold of poisoning of the carbonyl-containing polymeric resin is defined by an average α-amino-amide concentration in the reaction medium of the first stage below approximately 0.20 mole/l.

3. In a process in accordance with claim 1 for synthesizing an α-amino acid in the form of one of its salts from its corresponding α-amino-nitrile, or one of its salts, at a concentration of xM, the improvement wherein the fraction of the volume of the reaction medium of the second stage, withdrawn and recycled, is determined so that the α-amino-amide concentration in the medium of the first stage is substantially $(X/10)M$.

4. In a process in accordance with claim 3 for synthesizing an α-amino acid in the form of one of its salts at a concentration of 1M from its corresponding α-amino-nitrile, or one of its salts, the improvement wherein the fraction of the volume of the reaction medium of the second stage, withdrawn and recycled, is determined so that the α-amino-amide concentration in the reaction medium of the first stage is substantially decimolar.

5. Synthesis process as claimed in claim 1, wherein the hydroxide ions are introduced in the reaction medium of the second stage in a substantially equimolar amount relative to the α-amino-amide originating from the first stage.

6. Synthesis process as claimed in claim 1, wherein the amount of hydroxide ions needed for the catalysis originates from the recycling of a fraction of the reaction volume of the second stage.

* * * * *

UNITED STATES PATENT AND TRADEMARK OFFICE
CERTIFICATE OF CORRECTION

PATENT NO. : 4,677,224
DATED : June 30, 1987
INVENTOR(S) : Auguste Commeyras et al.

It is certified that error appears in the above-identified patent and that said Letters Patent is hereby corrected as shown below:

Column 8, line 12, "processor" should be --process for--.

Column 12, line 35, "$f_2[PH^-]_2$" should be --$f_2[OH^-]_2$--.

Column 13, at top of column, above the box containing the equation, insert the following two lines:

--$(f_3 - f_2 + f_o)[NH_3] - f_o[NH_3]_o = V \times k \times [OH-][Am]$ $(f_1 + f_o)[NH_3] - f_o[NH_3]_o = V \times k \times [OH-][Am]$--.

Column 13, line 35, above the box containing the equation, insert as a separate line --$(f_1 + f_o)[Ac] = f_o x_o - (d_o + d_1)[Am]$--.

Column 17, about lines 60-64, change the formula in the lower left of the reaction scheme to:

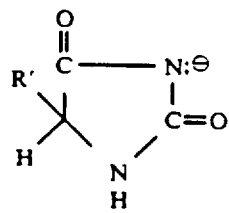

UNITED STATES PATENT AND TRADEMARK OFFICE
CERTIFICATE OF CORRECTION

PATENT NO. : 4,677,224
DATED : June 30, 1987
INVENTOR(S) : Auguste Commeyras et al.

Page 2 of 2

It is certified that error appears in the above-identified patent and that said Letters Patent is hereby corrected as shown below:

(changing "Ni" in the upper right corner of the formula to --N:--).

Column 18, in the Table beginning at line 10, move "4.08" and "5.31" to the left, under "3.26".

Signed and Sealed this

Twenty-sixth Day of April, 1988

Attest:

DONALD J. QUIGG

Attesting Officer

Commissioner of Patents and Trademarks